United States Patent [19]

Correa et al.

[11] Patent Number: 5,292,921

[45] Date of Patent: Mar. 8, 1994

[54] PROCESS FOR THE ENANTIOSELECTIVE PREPARATION OF PHENYLISOSERINE DERIVATIVES

[75] Inventors: Arlene Correa, Sao Carlos, Brazil; Jean-Noel Denis, Uriage, France; Andrew-Elliot Greene, Uriage, France; David S. Grierson, Magny les Hameaux, France

[73] Assignee: Rhone-Poulenc Rorer S.A., France

[21] Appl. No.: 946,448

[22] PCT Filed: May 21, 1991

[86] PCT No.: PCT/FR91/00405

§ 371 Date: Nov. 13, 1992

§ 102(e) Date: Nov. 13, 1992

[87] PCT Pub. No.: WO91/17976

PCT Pub. Date: Nov. 28, 1991

[30] Foreign Application Priority Data

May 22, 1990 [FR]  France .................. 90 06369

[51] Int. Cl.$^5$ ............................. C07C 269/00
[52] U.S. Cl. ........................... 560/29; 560/27; 562/444; 562/450
[58] Field of Search ............... 562/444, 450; 560/29, 560/27

[56] References Cited

U.S. PATENT DOCUMENTS

| | | | |
|---|---|---|---|
| 4,501,919 | 2/1985 | Koch et al. | 562/444 |
| 4,605,759 | 8/1986 | Mita et al. | 562/444 |
| 4,695,580 | 9/1987 | Ohashi et al. | 514/412 |

FOREIGN PATENT DOCUMENTS 253738 1/1988 European Pat. Off. .
336940 10/1989 European Pat. Off. .

OTHER PUBLICATIONS

Database WPIL, AN 83-31122k [13], Derwent Publications, Ltd., (London, GB), & JP-A-58 029 749, (H. Nohira), 22 Feb. 1983.

T. W. Greene, "Protective Groups in Organic Synthesis", 1981, pp. 16–22, 218–221, 261–263, Wiley-Interscience Pub., John Wiley & Sons.

The Journal of Organic Chemistry, vol. 49, No. 4, 24 Feb. 1984, American Chemical Society, Marx, et al.: "Reactivity-selectivity in the swern oxidation of alcohols using dimethyl sulfoxide-oxalyl chloride", pp. 788–793.

A. H. Haines: "Methods for the Oxidation of Organic Compounds", 1985, pp. 126–130, Academic Press, (London, GB).

The Journal of Organic Chemistry, v. 51, No. 1, 10 Jan. 1986, American Chem. Society, N. N. Denis, et al "An efficient, enantioselective synthesis of the taxol side chain", pp. 46–50.

Journal of the American Chemical Society, v. 110, No. 17, 17 Aug. 1988 Denis, et al., "A highly efficient, practical approach to natural taxol"; pp. 5917–5919.

Primary Examiner—José G. Dees
Assistant Examiner—Samuel Barts
Attorney, Agent, or Firm—Morgan & Finnegan

[57] ABSTRACT

Process for the enantioselective preparation of phenylisoserine derivatives of general formula (I)

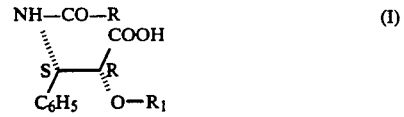

from phenylglycine S(+) wherein R is a phenyl radical or a tert butoxy radical and R is an alcohol protective group.

10 Claims, No Drawings

PROCESS FOR THE ENANTIOSELECTIVE PREPARATION OF PHENYLISOSERINE DERIVATIVES

FIELD OF THE INVENTION

The present invention relates to a process for the enantioselective preparation of phenylisoserine derivatives of the general formula

DESCRIPTION OF THE INVENTION

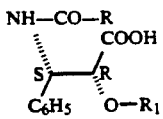

in which R is a phenyl radical or a tert-butoxy radical and $R_1$ is a protecting group for the hydroxyl group.

In general formula (I), $R_1$ is more particularly a methoxymethyl, 1-ethoxyethyl, benzyloxymethyl, (b-trimethylsilylethoxy)methyl, tetrahydropyranyl or 2,2,2-trichloroethoxycarbonyl radical. The radical $R_1$ is preferably the 1-ethoxyethyl radical.

The products of general formula (I) are useful for preparing the baccatin III and 10-deacetylbaccatin III derivatives of the general formula

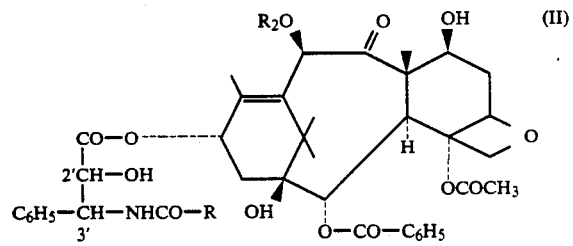

in which R is a phenyl radical or a tert-butoxy radical and $R_2$ is a hydrogen atom or an acetyl radical.

The products of general formula (II) in which R is a phenyl radical correspond to taxol and 10-deacetyltaxol and the products of general formula (II) in which R is a tert-butoxy radical correspond to those described in European patent 253 738.

The products of general formula (II), and in particular the product of general formula (II) in which $R_2$ is a hydrogen atom and which is in the 2′R,3′S form, have particularly valuable antitumoural and antileukaemic properties.

The products of general formula (II) can be obtained by reacting a product of general formula (I) with a taxane derivative of the general formula

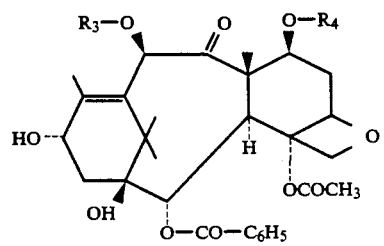

in which $R_3$ is an acetyl radical or a protecting group for the hydroxyl group and $R_4$ is a protecting group for the hydroxyl group, and then replacing the protecting groups $R_1$ and $R_4$ and, if appropriate, $R_3$ with a hydrogen atom under the conditions described by J-N. DENIS et al., J. Amer. Chem. Soc., 110(17) 5917–5919 (1988).

According to the present invention, the products of general formula (I) are obtained from S(+)-phenylglycine of the formula

by treatment with a reducing agent and with a reagent for introducing a benzoyl or t-butoxycarbonyl group to give the alcohol of the formula

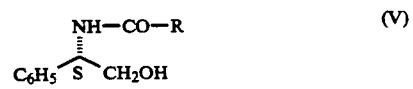

in which R is a phenyl or tert-butoxy radical, which is oxidized and then reacted with a vinylmagnesium halide to give the product of the formula

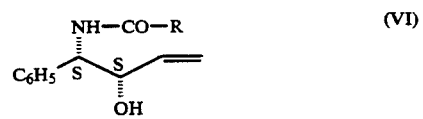

in which R is a phenyl or tert-butoxy radical, the hydroxyl group of which is then protected by a group $R_1$ to give a product of the general formula

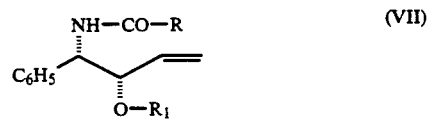

in which R is a phenyl or tert-butoxy radical and $R_1$ is as defined above, which is oxidized to the product of general formula (I).

According to the invention, the alcohol of formula (V) can be obtained:
- either by reacting an agent for introducing a benzoyl or t-butoxycarbonyl group with the amino alcohol obtained by reducing S(+)-phenylglycine,
- or by reacting a reducing agent with the acid obtained by reacting an agent for introducing a benzoyl or t-butoxycarbonyl group with S(+)-phenylglycine.

Whichever variant of the process is used, it is not necessary to isolate the amino alcohol or the acid formed as an intermediate.

To carry out the process, it is particularly advantageous to reduce the S(+)-phenylglycine and then to react the product with the agent for introducing a benzoyl or t-butoxycarbonyl group.

As the reducing agent, it is preferred to use lithium aluminum hydride or borane ($BH_3$), preferably in the form of a complex with dimethyl sulphide, in the presence of boron trifluoride etherate. The reaction is generally carried out in an inert organic solvent such as, for example, an ether like tetrahydrofuran or dimethoxyethane. The reduction is generally carried out at a temperature of between 50° and 100° C.

As the agent for introducing a benzoyl or t-butoxycarbonyl group, it is preferred to use benzoyl chloride or di-t-butyl dicarbonate, as the case may be. The reaction is generally carried out in an organic solvent such as methylene chloride, in the presence of an inorganic base such as sodium hydroxide or sodium bicarbonate or carbonate, or an organic base such as triethylamine or 4-dimethylaminopyridine. The reaction is generally carried out at between 0° C. and the reflux temperature of the reaction mixture.

According to the invention, the alcohol of formula (VI) is obtained by reacting a vinylmagnesium halide with the aldehyde obtained by selective oxidation of the alcohol of formula (V).

The oxidation of the alcohol of formula (V) is generally carried out by means of an oxalyl chloride/dimethyl sulphoxide mixture at a temperature below 0° C., in an organic solvent such as methylene chloride or tetrahydrofuran, in the presence of an organic base such as triethylamine or diisopropylethylamine.

The alcohol of formula (VI) is obtained by adding the aldehyde to a solution of a vinylmagnesium halide, preferably vinylmagnesium bromide, in an inert organic solvent such as tetrahydrofuran, mixed with methylene chloride if appropriate. It is not necessary to isolate the intermediate aldehyde produced by oxidation of the alcohol of formula (V).

This procedure essentially gives the alcohol of formula (VI) in the syn form with an enantiomeric excess of more than 99%.

The product of general formula (VII) can be obtained from the alcohol of formula (VI) under the normal conditions for the preparation of ethers and acetals, for example in accordance with the processes described by J-N. DENIS et al., J. Org. Chem., 51, 46-50 (1986).

The product of general formula (I) is obtained by oxidizing the alcohol of general formula (VII). It is particularly advantageous to carry out the oxidation by means of an alkali metal periodate (sodium periodate), in the presence of a catalytic amount of a ruthenium salt ($RuCl_3$) and sodium bicarbonate, in an aqueous-organic medium such as, for example, an acetonitrile/carbon tetrachloride/water mixture. The reaction is generally carried out at a temperature of about 20° C.

The oxidation can also be carried out by means of potassium permanganate, for example in the presence of adogen in a pentane/water mixture or in the presence of aliquat or dicylohexyl-18-crown-6 in methylene chloride or in a pyridine/water mixture. It is also possible to use triethylbenzylammonium permanganate in the presence of pyridine in methylene chloride.

The process according to the invention makes it possible to obtain the product of general formula (I) diastereoselectively and enantioselectively, said product being directly usable in the synthesis of therapeutically valuable products.

EXAMPLES

The following Examples, which are given without implying a limitation, show how the invention can be put into practice.

EXAMPLE 1

A suspension of 4.55 g (120 mmol) of lithium aluminum hydride in 210 cm³ of anhydrous tetrahydrofuran is introduced under an argon atmosphere into a 500 cm³ round-bottomed flask equipped with a magnetic stirring system and a condenser. The suspension is heated to the reflux temperature and 9.07 g (60 mmol) of S(+)-phenylglycine are then added in small fractions over a period of 15 minutes. The condenser is rinsed with 10 cm³ of tetrahydrofuran and the mixture is refluxed for 6 hours.

After cooling to a temperature of about 20° C., 7.28 cm³ of a 10% (w/v) aqueous solution of sodium hydroxide and 9.12 cm³ of water are added slowly. The reaction is left to proceed for 5 minutes and a solution of 14.40 g (66 mmol) of di-t-butyl dicarbonate in 80 cm³ of methylene chloride and 200 mg (1.64 mmol) of 4-dimethylaminopyridine are then added. The reaction mixture is refluxed for 6 hours. After cooling to a temperature of about 20° C, the heterogeneous reaction mixture is filtered under reduced pressure over anhydrous sodium sulphate. The solids are washed 4 times with 30 cm³ of methylene chloride. The solvents are driven off under reduced pressure on a rotary evaporator. The residue obtained (15.95 g) is dissolved hot in 80 cm³ of methylene chloride. 350 cm³ of cyclohexane are added and the product is left to crystallize. After filtration under reduced pressure, 7.503 g (31.7 mmol) of S(+)-2-phenyl-2-t-butoxycarbonylaminoethanol are obtained in the form of white crystals.

The residue obtained after concentration of the mother liquors of crystallization is chromatographed on a column of silica gel. Elution with an ether/hexane mixture (1/1 by volume) gives 2.986 g (12.6 mmol) of S(+)-2-phenyl-2-t-butoxycarbonylaminoethanol.

The overall yield is 74%.

S(+)-2-Phenyl-2-t-butoxycarbonylaminoethanol has the following characteristics:

melting point: 136°-137° C. (after recrystallization from a methylene chloride/cyclohexane mixture)

optical rotation: $[a]^{24}_D = +39.6°$ (c=1.64; chloroform)

infrared spectrum (film): principal absorption bands at 3300, 3250, 3050, 2980, 2900, 1670, 1580, 1555, 1490, 1450, 1365, 1340, 1315, 1290, 1230, 1180, 1102, 1070, 1060, 1040, 1030, 865, 840, 760 and 700 cm$^{-1}$ proton nuclear magnetic resonance spectrum (300 MHz; $CDCl_3$; chemical shifts in ppm; coupling constants J in Hz): 1.43 (s, 9H); 1.99 (s broad, 1H); 3.85 (d, J=4.3, 2H); 4.77 (s broad, 1H); 5.20 (s broad, 1H); 7.26–7.38 (m, 5H)

$^{13}C$ nuclear magnetic resonance spectrum ($CDCl_3$): 28.24 (3×$CH_3$); 56.70 (CH); 66.60 ($CH_2$); 79.91 (C); 126.47 (CH); 127.59 (CH); 128.64 (CH); 139.63 (C) and 156.08 (C)

mass spectrum (c.i.) ($NH_3$+isobutane): 295 (M+ +isobutane); 255 (MH+ +$NH_3$); 238 (MH+) parent peak; 220, 206, 199, 182, 168, 150, 138, 124 and 106 elemental analysis: calculated C 65.80 H 8.07 N 5.90. found C 65.89 H 8.02 N 5.76

EXAMPLE 2

24 cm³ of anhydrous methylene chloride are introduced under an argon atmosphere into a 100 cm³ single-necked flask equipped with a magnetic stirring system. It is cooled to −78° C. and 1.05 c³ (12 mmol) of pure oxalyl chloride are then added. The solution is stirred for 5 minutes at −78° C. and 908 μl (12.8 mmol) of pure dimethyl sulphoxide are then added all at once. The reaction is instantaneous and gas is evolved. The solution is left to react for 5 minutes at 78° C. and the temperature is then allowed to rise to 60° C. over a period of 20 minutes. A solution of 1.896 g (8 mmol) of S(+)-2-phenyl-2-t-butoxycarbonylaminoethanol in 24 cm³ of dry anhydrous methylene chloride is added over a period of 15 minutes. The round-bottomed flask which contained the alcohol is rinsed with 2 cm³ of methylene chloride. The temperature is then allowed to rise to −35° C. over a period of 20 minutes. The reaction is left to proceed for 5 minutes at this temperature and 8.36 cm³ (48 mmol) of pure diisopropylethylamine are then added over a period of 4 minutes. The temperature is allowed to rise to 5°–0° C. over a period of 10 minutes and the resulting yellow homogeneous solution (containing the aldehyde) is then transferred over a period of 4 minutes into 104 cm³ of a 0.5M solution of vinylmagnesium bromide in a tetrahydrofuran/methylene chloride mixture (1/1 by volume). The reaction is exothermic and a condenser must be used. When the addition is complete, the resulting homogeneous solution is left to react for 1 hour at a temperature of about 20° C. and 8 cm³ of ethanol and 12 cm³ of a saturated aqueous solution of ammonium chloride are then added successively. 100 cm³ of methylene chloride and 100 cm³ of a 2M aqueous solution of hydrochloric acid are added to the heterogeneous mixture in order to solubilize the solids present. The two phases obtained are separated. The aqueous phase is extracted 3 times with 50 cm³ of methylene chloride. The organic phases are combined and washed twice with 50 cm³ of water and once with 50 cm³ of a saturated aqueous solution of sodium chloride. The aqueous phases are combined and then extracted a further twice with 50 cm³ of methylene chloride. The resulting organic phases are combined and then washed twice with 20 cm³ of water and 20 cm³ of a saturated aqueous solution of sodium chloride. All the organic phases are combined and then dried over anhydrous sodium sulphate. They are then filtered under reduced pressure on Célite and the solvents are driven off on a rotary evaporator. The residue obtained (3.75 g) is purified on a column containing 500 cm³ of silica gel. Elution with an ether/methylene chloride mixture (5/95 by volume) gives 1.70 g (6.46 mmol) of a mixture of the syn and anti forms of 1-phenyl-1-t-butoxycarbonylamino-2-hydroxybut-3-ene in a ratio of 94/6. The yield is 81%. The two diastereoisomers are separated by chromatography on a column of silica gel using an ether/ methylene chloride/hexane mixture (5/45/50 by volume) as the eluent. 1.304 g (4.96 mmol) of pure 1-phenyl-1-t-butoxycarbonylamino-2-hydroxybut-3-ene (1S,2S) are obtained with a yield of 62%, its characteristics being as follows:

melting point: 56°–57° C.
optical rotation: $[a]^{25}_D = +0.3°$ (c=1.58, chloroform)
infrared spectrum (film): principal absorption bands at 3400, 2975, 2920, 1690, 1500, 1450, 1390, 1365, 1250, 1175, 1080, 1050, 1020, 995, 920, 755 and 700 cm¹
proton nuclear magnetic resonance spectrum (300 MHz; CDCl₃; chemical shifts in ppm; coupling constants J in Hz): 1.40 (s, 9H); 1.9 (s broad, 1H); 4.38 (pst, J=4.6 and 4.8, 1H); 4.70 (s broad, 1H); 5.20 (dt, J=1.4 and 10.5, 1H); 5.26 (s broad, 1H); 5.34 (dt, J=1.4 and 17.2, 1H); 5.86 (ddd, J=5.4, 10.5 and 17.2, 1H); 7.24–7.37 (m, 5H)
¹³C nuclear magnetic resonance spectrum (CDCl₃): 28.12 (3×CH₃); 58.74 (CH); 75.33 (CH); 79.58 (C); 116.36 (CH₂); 126.69 (CH); 127.26 (CH); 128.32 (CH); 137.17 (CH); 139.96 (C); 155.89 (C)

mass spectrum (c.i.) (NH₃+isobutane): 321 (M⁺+isobutane); 281 (MH⁺+NH₃); 264 (MH⁺) parent peak; 246, 225, 208, 190, 164, 124 and 106
elemental analysis: calculated C 68.41 H 8.04 N 5.32. found C 68.15 H 7.98 N 5.34.

EXAMPLE 3

1.045 g (3.97 mmol) of 1-phenyl-1-t-butoxycarbonylamino-2-hydroxybut-3-ene (1S,2S), 20 cm³ of anhydrous methylene chloride, 3.8 cm³ (39.7 mmol) of distilled ethyl vinyl ether and 99 mg (0.397 mmol) of pyridinium p-toluenesulphonate are introduced successively into a 50 cm³ single-necked flask placed under an argon atmosphere and equipped with a magnetic stirring system. The reaction is left to proceed for 4 hours at a temperature of about 20° C. When the reaction is complete, 1 drop of pyridine is added and the reaction mixture is then diluted in methylene chloride. The organic phase is washed twice with water and twice with a saturated aqueous solution of sodium chloride and then dried over anhydrous sodium sulphate. After filtration, the solvents are driven off under reduced pressure on a rotary evaporator. The residue obtained (1.545 g) is purified on a column of silica gel using a hexane/ether mixture (80/20 by volume) as the eluent. 1.191 g (3.56 mmol) of 1-phenyl-1-t-butoxycarbonylamino-2-(1-ethoxyethoxy)but-3-ene (1S,2with a yield of 90% in the form of two epimers in a ratio of 55/45.

1-Phenyl-1-t-butoxycarbonylamino-2-(1-ethoxyethoxy)but-3-ene (1S,2S) has the following characteristics:

melting point: 59°–65° C.
optical rotation: $[a]^{25}_D = +14.9°$ (c=1.64, chloroform)
infrared spectrum (film): principal absorption bands at 3370, 2970, 2925, 2875, 1680, 1520, 1495, 1365, 1285, 1250, 1170, 1080, 1050, 1005, 955, 930, 890, 870, 755 and 705 cm⁻¹
proton nuclear magnetic resonance spectrum (300 MHz; CDCl₃; shifts in ppm; coupling constants J in Hz): 0.9 (min) and 1.07 (maj) (2t, J=7.0, 3H); 1.05 (min) and 1.22 (maj) (2d, J=5.3 (min) and 5.4 (maj), 3H); 1.40 (s, 9H); 2.90–2.98 and 3.05–3.51 (m, 2H); 4.16 and 4.23 (2psdd, J=6.6 and 7, 1H); 4.31 (min) and 4.62 (maj) (2q, J=5.3 (min) and 5.4 (maj), 1H); 4.71 (maj) and 4.73 (min) (2m, 1H); 5.22 and 5.23 (2dt, J=1.2 and 10.5, 1H); 5.25 and 5.30 (2dt, J=1.2 and 17.4, 1H); 5.37 and 5.44 (2m, 1H); 5.77 (min) and 5.91 (maj) (2ddd, J=7, 10.5 and 17.4, 1H); 7.17–7.37 (m, 5H)
elemental analysis: calculated C 68.03 H 8.71 N 4.18. found C 68.00 H 8.78 N 4.13.

EXAMPLE 4

A solution of 1.09 g (3.25 mmol) of the product obtained in Example 3 in 6.5 cm³ of acetonitrile is introduced into a 50 cm³ single-necked round-bottomed flask placed under an argon atmosphere and equipped with a magnetic stirring system. 6.5 cm³ of carbon tetrachloride, 9.8 cm³ of distilled water and, with vigorous stirring, 1.774 g (21.125 mmol) of sodium bicarbonate are then added successively. 3.824 g (17.875 mmol) of sodium periodate are then added in small portions. The reaction is left to proceed for 5 minutes, with stirring (evolution of gas), and 109 mg of ruthenium chloride are then added all at once. The reaction is left to proceed for 48 hours at a temperature of about 20° C., with vigorous stirring.

The reaction mixture is diluted with water to give a total volume of 40 cm³. The black basic aqueous phase is extracted 3 times with 40 cm³ of ether. The basic phase is then cooled to 0° C., after which it is treated dropwise with 12.9 cm³ of a 2M aqueous solution of hydrochloric acid, in the presence of 120 cm³ of methylene chloride, with vigorous stirring. The resulting acidic aqueous phase is extracted 8 times with 120 cm³ of methylene chloride. The organic phases are combined and washed with 3 times 40 cm³ of water and 1 times 40 cm³ of a saturated aqueous solution of sodium chloride. They are died over a sodium sulphate/magnesium sulphate mixture (1/1) and filtered under reduced pressure over Celite. The solvents are driven off under reduced pressure until a volume of 5 to 8 cm³ is obtained. The residue is dried over a 4 Å molecular sieve. The liquid phase is separated from the molecular sieve and the remaining solvent is then driven off on a rotary evaporator.

940 mg (2.663 mmol) of pure 3-phenyl-3-t-butoxycarbonylamino-2-(1-ethoxyethoxy)propionic acid (2R,3S) are obtained in the form of a pale yellow oil. The yield is 82%.

3-Phenyl-3-t-butoxycarbonylamino-2-(1-ethoxyethoxy)propionic acid (2R,3S) has the following characteristics:

optical rotation: $[a]^{25}_D = +17.6°$ (c=1.16, chloroform)

infrared spectrum (film): principal absorption bands at 3700-2200, 3060, 2980, 2930, 2850, 1720, 1660, 1602, 1590, 1500, 1450, 1400, 1370, 1280, 1250, 1170, 1080, 1050, 1030, 955, 930, 890 and 700 cm$^{-1}$ proton nuclear magnetic resonance spectrum (300 MHz; CDCl₃; chemical shifts in ppm; coupling constants J in Hz): 0.81 and 1.04 (2t, J=7, 3H); 1.18 and 1.20 (2d, J=5.4, 3H); 1.42 (s, 9H); 2.60-2.88 and 3.15-3.52 (m, 2H); 4.35-4.50 and 4.65-4.80 (m, 2H); 5.29 (s broad, 1H); 5.72 (s broad, 1H); 7.13-7.38 (m, 5H); 8.52 (s broad, 1H)

EXAMPLE 5

3.605 g (23.85 mmol) of S(+)-phenylglycine and 22.5 cm³ of anhydrous dimethoxyethane are introduced under an argon atmosphere into a 100 cm³ two-necked round-bottomed flask surmounted by a condenser and equipped with a thermometer and a magnetic stirrer. The suspension obtained is heated to 72°-73° C. and 3.6 cm³ (29.07 mmol) of boron trifluoride etherate distilled over calcium hydride are then added dropwise over a period of 15 minutes. When the addition is complete, the resulting yellow homogeneous solution is heated at 68°-70° C. for one hour. This reaction mixture is then heated to 77°-78° C., after which 3.82 cm³ (38.2 mmol) of a 10M solution of Me₂S.BH₃ in tetrahydrofuran are added slowly over a period of about 5 minutes. The reaction is left to proceed for 4 hours under reflux and the final reaction medium is cooled to a temperature of about 20° C. 3.6 cm³ (88.9 mmol) of dry methanol are then added very slowly so that the temperature of the reaction medium does not exceed 40° C.

This reaction medium is then heated to the reflux temperature so as to reduce the volume by about half, after which 13 cm³ of a 6N aqueous solution of sodium hydroxide (77.8 mmol) are added very slowly. The mixture is heated at 85° C. for 30 minutes.

It is subsequently cooled to 0° C. and 13 cm³ of methylene chloride are then added. 24 cm³ of a solution of 5.73 g (26.23 mmol) of di-t-butyl dicarbonate in methylene chloride are then added and the reaction is left to proceed at 0° C. for 18 hours.

Methylene chloride and water are added. The aqueous and organic phases are separated. The aqueous phase is extracted 4 times with 30 to 40 cm³ of methylene chloride. The organic phases are combined, washed twice with 10 cm³ of a 2M aqueous solution of hydrochloric acid, twice with 20 cm³ of water and once with a saturated aqueous solution of sodium chloride and then dried over anhydrous sodium sulphate. After filtration, the solvents are driven off under reduced pressure. The solid residue (5.43 g) is dissolved hot in the minimum volume of methylene chloride (30 cm³), and 76 cm³ of cyclohexane are then added to the resulting solution. The product is left to crystallize. After filtration under reduced pressure, 2.686 g (11.3 mmol) of S(+)-2-phenyl-2-t-butoxycarbonylaminoethanol are obtained in the form of white crystals. Crystallization of the residue of the mother liquors from the same solvent system (minimum volume of CH₂Cl₂/cyclohexane) yields a further 1.1 g (4.6 mmol) of the alcohol in the form of white crystals. The residue of the mother liquors is then purified on a column of silica gel using an ether/hexane mixture (30/70 by volume) as the eluent. 0.315 g (1.33 mmol) of the alcohol is thus obtained.

The overall yield is 72%.

The product obtained is identical to that obtained in Example 1.

EXAMPLE 6

2.52 g (66 mmol) of lithium aluminum hydride and 120 cm³ of anhydrous tetrahydrofuran are introduced under argon into a 500 cm³ single-necked flask equipped with a magnetic stirring system and surmounted by a condenser. The resulting suspension is heated to the reflux temperature (external temperature 80° C) and 5.0 g (33 mmol) of S(+)-phenylglycine are then added in small portions over a period of 15 minutes. The reaction mixture is then refluxed for 6 hours. It is left to cool to a temperature of about 20° C. and 4 cm³ of a 10% (w/v) aqueous solution of sodium hydroxide are then added slowly, followed by 5 cm³ of water. The reaction is left to proceed for 5 minutes, a further 53 cm³ of the 10% (w/v) aqueous solution of sodium hydroxide are then added and 3.3 cm³ (28 mmol) of benzoyl chloride are then introduced at 0° C. The reaction is left to proceed for 30 minutes at a temperature of about 20° C. When the reaction is complete, the reaction mixture is diluted in 200 cm³ of methylene chloride, and 100 cm³ of a saturated aqueous solution of potassium sodium tartrate (Rochele salt) are added. After stirring, the two phases are separated. The aqueous phase is washed u twice with 50 cm³ of methylene chloride. The combined organic phases are washed 3 times with 20 cm³ of water, once with a 5% aqueous solution of hydrochloric acid and twice with a saturated aqueous solution of sodium chloride and then dried over anhydrous sodium sulphate. After filtration, the solvents are driven off under reduced pressure. The solid residue obtained is dissolved hot in 400 cm³ of methylene chloride and 15 cm³ of methanol and then left to crystallize. After filtration, 4.9 g (20.3 mmol) of S(-)-2-phenyl-2-benzoylaminoethanol are obtained with a yield of 62% in the form of white crystals. The residue obtained after concentration of the mother liquors (2.5 g) is chromatographed on a column of silica gel. Elution with a methylene chloride/ethyl acetate mixture (8/2 by volume) gives 1.418 g (5.88 mmol) of S(−)-2-phenyl-2-benzoylaminoethanol. The overall yield based on S(+)-phenylglycine is 79%.

S(−)-2-Phenyl-2-benzoylaminoethanol has the following characteristics:

melting point: 179°-180° C. (after recrystallization from a methylene chloride/cyclohexane mixture)

optical rotation: $[\alpha]^{25}_D = -17.8°$ (c=1.48, methanol)

infrared spectrum (film): principal characteristic absorption bands at 3300, 1630, 1600, 1580, 1520, 1310, 1290, 1265, 1120, 1075, 1040, 1030, 880, 840, 800, 750 and 700 cm$^{-1}$ proton nuclear magnetic resonance spectrum (300 MHz; CDCl$_3$; chemical shifts in ppm; coupling constants J in Hz): 2.40 (t, J=5.5, 1H); 3.93 (dd, J=4.8 and 5.5, 2H); 5.18 (dt, J=4.8 and 6.5, 1H); 6.71 (s broad, 1H); 7.16–7.42 (m, 8H); 7.70–7.73 (m, 2H)

$^{13}$C nuclear magnetic resonance spectrum (CDCl$_3$+CD$_3$OD): 55.78 (CH); 65.29 (CH$_2$); 126.59 (CH); 127.01 (CH); 127.48 (CH); 128.40 (CH); 128.53 (CH); 131.58 (CH); 134.01 (C); 139.22 (C); 166.17 (C)

mass spectrum (c.i.) (NH$_3$+isobutane): 242 (MH+); 224 (M+—OH); 210 (M+—CH$_2$OH); 122; 105 (C$_6$H$_5$CO+)

elemental analysis: calculated C 74.66 H 6.27 N 5.81. found C 74.45 H 6.10 N 5.91

EXAMPLE 7

16 cm$^3$ of dry methylene chloride are introduced into a 100 cm$^3$ two-necked round-bottomed flask placed under an argon atmosphere and equipped with a magnetic stirring system. It is cooled to −78° C. and 1.05 cm$^3$ (12 mmol) of pure oxalyl chloride are then added. The solution is stirred for 5 minutes at −78° C. and 0.908 cm$^3$ (12.8 mmol) of pure dimethyl sulphoxide is then added all at once. The reaction is instantaneous and gas is evolved. The reaction is left to proceed for 5 minutes at −78° C. and the temperature is then allowed to rise to −60° C. over a period of 20 minutes. A suspension of 1.881 g (7.8 mmol) of S(-)-2-phenyl-2-benzoylaminoethanol in 25 cm$^3$ of a methylene chloride/dimethyl sulphoxide mixture (24/1 by volume) is added over a period of 15 minutes. The round-bottomed flask which contained this suspension is rinsed with 5 cm$^3$ of methylene chloride and the temperature of the resulting reaction mixture is then allowed to rise to −35° C. over a period of 20 minutes. The reaction is left to proceed at this temperature for 5 minutes and 8.36 cm$^3$ (48 mmol) of pure diisopropylethylamine are then added over a period of 4 minutes. The temperature is allowed to rise for 5 minutes and the mixture is then cooled to 78° C. The homogeneous reaction mixture (containing the aldehyde) is stirred for 5 minutes at this temperature and then transferred into 104 cm$^3$ of a solution (0.5M) of vinylmagnesium bromide in a tetrahydrofuran/methylene chloride mixture (1/1 by volume). The reaction is exothermic and a condenser must be used. When the addition is complete, the resulting homogeneous solution is left to react for 1 hour at a temperature of about 20° C. and 8 cm$^3$ of ethanol and 12 cm$^3$ of saturated aqueous solution of ammonium chloride are then added successively. 100 cm$^3$ of methylene chloride and 100 cm$^3$ of 2M hydrochloric acid are added to the heterogeneous mixture in order to solubilize the solids. The two phases obtained are separated. The aqueous phase is extracted 3 times with 50 cm$^3$ of methylene chloride. The organic phases are combined and then washed twice with 20 cm$^3$ of water and once with 20 cm$^3$ of a saturated aqueous solution of sodium chloride. They are dried over anhydrous sodium sulphate. After filtration, the solvents are driven off under reduced pressure on a rotary evaporator. The residue obtained (2.85 g) is chromatographed on a column of silica gel. Elution with a methylene chloride/ethyl acetate mixture (95/5 by volume) gives 1-phenyl-1-benzoylamino-2-hydroxybut-3-ene, syn form, with a yield of 56% (1.168 g, 4.37 mmol) and 1-phenyl-1-benzoylamino-2-hydroxybut-3-ene, anti form, with a yield of 13% (0.28 g, 1.05 mmol). 169 mg (0.7 mmol, 9%) of the starting material, S(−)-2-phenyl-2-benzoylaminoethanol, are recovered.

1-Phenyl-1-benzoylamino-2-hydroxybut-3-ene, syn form, has the following characteristics:

melting point: 135°-136° C. (after recrystallization from a methylene chloride/cyclohexane mixture)

optical rotation: $[\alpha]^{23}_D = -49.9°$ (c=1.035, chloroform)

infrared spectrum (film): principal characteristic absorption bands at 3300, 1620, 1525, 1510, 1335, 1295, 1120, 1080, 995, 920 and 700 cm$^{-1}$ proton nuclear magnetic resonance spectrum (200 MHz; CDCl$_3$; chemical shifts in ppm; coupling constants in Hz): 2.40 (d, J=3.9, 1H); 4.55 (ddd, J=3.5, 3.5 and 5, 1H); 5.23 (dt, J=1.5 and 10.5, 1H); 5.26 (dd, J=3.5 and 7.6, 1H); 5.40 (dt, J=1.5 and 17.1, 1H); 5.94 (ddd, J=5, 10.5 and 17.1, 1H); 6.98 (d, J=7.6, 1H); 7.24–7.54 (m, 8H); 7.80–7.83 (m, 2H)

$^{13}$C nuclear magnetic resonance spectrum (CDCl$_3$) 57.71 (CH); 75.31 (CH); 116.58 (CH$_2$); 126.89 (CH); 127.04 (CH); 127.68 (CH); 128.56 (CH); 128.72 (CH); 131.60 (CH); 134.31 (C); 137.41 (CH); 139.60 (C); 167.54 (C)

mass spectrum (c.i.) (NH$_3$+isobutane): 268 (MH+); 250 (M+—OH); 210; 105 (C$_6$H$_5$CO+)

1-Phenyl-1-benzoylamino-2-hydroxybut-3-ene, anti form, has the following characteristics:

melting point: 176°-177° C. (after recrystallization from a methylene chloride/cyclohexane mixture)

optical rotation: $[\alpha]^{23}_D = -16.8°$ (c=1.1, chloroform)

infrared spectrum (in liquid paraffin): principal characteristic absorption bands at 3300, 1620, 1580, 1520, 1450, 1300, 1115, 1080, 1060, 1035, 985, 920, 870, 820, 800, 750 and 700 cm$^{-1}$ proton nuclear magnetic resonance spectrum (200 MHz; CDCl$_3$; chemical shifts in ppm; coupling constants J in Hz): 2.43 (s broad, 1H); 4.60 (m, 1H); 5.23 (dt, J=1.5 and 10.4, 1H); 5.33 (dd, J=4 and 8, 1H); 5.34 (dt, J=1.5 and 17, 1H); 5.79 (ddd, J=5, 10.4 and 17, 1H); 6.88 (d, J=8, 1H); 7.3–7.54 (m, 8H); 7.78–7.82 (m, 2H)

$^{13}$C nuclear magnetic resonance spectrum (CDCl$_3$): 58.23 (CH); 75.28 (CH); 117.29 (CH$_2$); 126.94 (CH); 127.52 (CH); 127.80 (CH); 128.53 (CH); 128.58 (CH); 131.64 (CH); 134.14 (C); 136.30 (CH); 137.56 (C); 167.23 (C)

mass spectrum (c.i.) (NH$_3$+isobutane): 268 (MH+); 250 (M+—OH); 210; 105 (C$_6$H$_5$CO+)

EXAMPLE 8

708 mg (2.65 mmol) of 1-phenyl-1-benzoylamino-2-hydroxybut-3-ene, syn form, 13.5 cm$^3$ of dry methylene chloride, 2.53 cm$^3$ (1.911 g, 26.5 mmol) of ethyl vinyl ether and 66.5 mg (0.265 mmol) of pyridinium p-toluenesulphonate (PPTS) are introduced successively into a 50 cm³ single-necked flask placed under an argon atmosphere and equipped with a magnetic stirring system. The resulting homogeneous reaction mixture is left to react for 4 hours at a temperature of about 20° C. When the reaction is complete, 1 drop of pyridine is added and the reaction mixture is then diluted in 20 cm³ of methylene chloride. The organic phase is washed once with 20 cm³ of water. The aqueous phase is extracted twice with 20 cm³ of methylene chloride. The combined organic phases are washed twice with 20 cm³ of water and once with 10 cm³ of a saturated aqueous solution of sodium chloride and then dried over anhydrous sodium sulphate. After filtration, the solvents are driven off under reduced pressure on a rotary evaporator. The residue obtained (992 mg) is chromatographed on a column of silica gel. Elution with a hexane/ether mixture (6/4 by volume) gives 1-phenyl-1-benzoylamino-2-(1-ethoxyethoxy)but-3-ene, syn form, with a yield of 91% (818 mg, 2.41 mmol). The product obtained is in the form of an equimolar mixture of the two epimers (determination by the proton nuclear magnetic resonance spectrum).

1-Phenyl-1-benzoylamino-2-(1-ethoxyethoxy)but-3-ene, syn form, has the following characteristics:
  melting point: 85.5°–87° C.
  optical rotation: $[\alpha]^{22}_D = -34.4°$ (c=1.6, chloroform)
  infrared spectrum (film): principal characteristic absorption bands at 3300, 2975, 2920, 2870, 1630, 1600, 1580, 1520, 1485, 1320, 1125, 1080, 1030, 990, 920 and 700 cm$^{-1}$
  proton nuclear magnetic resonance spectrum (200 MHz; CDCl₃; chemical shifts in ppm; coupling constants J in Hz): 1.00 and 1.08 (2t, J=7, 3H); 1.09 and 1.29 (2d, J=5.3, 3H); 2.98–3.56 (m, 2H); 4.36 and 4.66 (2q, J=5.3, 1H); 4.29–4.43 (m, 1H); 5.12–5.46 (m, 3H); 5.81 and 5.99 (2ddd, J=6.5, 10.4 and 17.1, 1H); 7.05 (d, J=8, 1H); 7.15–7.55 (m, 8H); 7.74–7.92 (m, 2H)
  mass spectrum (c.i.) (NH₃+isobutane): 340 (MH⁺); 294, 268, 250, 211, 105 (C₆H₅CO⁺)

EXAMPLE 9

A solution of 254 mg (0.75 mmol) of 1-phenyl-1-benzoylamino-2-(1-ethoxyethoxy)but-3-ene, syn form, in 1.5 cm³ of acetonitrile is introduced into a 15 cm³ single-necked flask placed under an argon atmosphere and equipped with a magnetic stirring system. 1.5 cm³ of carbon tetrachloride, 2.25 cm³ of distilled water and, with thorough stirring, 409.5 mg (4.875 mmol) of solid sodium bicarbonate are then added successively. 882 mg (4.125 mmol) of sodium periodate are then added in small portions. The heterogeneous reaction medium is left to react for 5 minutes (evolution of gas) and 25.4 mg (10% by weight) of RuCl₃ (Aldrich) are then added all at once. The heterogeneous reaction mixture, which has turned black, is left to react for 48 hours at a temperature of about 20° C, with vigorous stirring.

When the reaction is complete, the reaction mixture is diluted with water to give a total volume of 12 cm³. The black basic aqueous phase is extracted 3 times with 20 cm³ of ether. The basic phase is then cooled to 0° C., after which it is treated dropwise with 3 cm³ of a 2M aqueous solution of hydrochloric acid, in the presence of 30 cm³ of methylene chloride, with vigorous stirring. The resulting acidic aqueous phase is extracted 8 times with 35 cm³ of methylene chloride. The organic phases are combined and washed with 3 times 8 cm³ of water and 1 times 10 cm³ of a saturated aqueous solution of sodium chloride. They are dried over a sodium sulphate/magnesium sulphate mixture (1/1 by weight) and filtered under reduced pressure on Célite. The solvents are driven off under reduced pressure until concentration of a volume of 5 to 10 cm³. This is dried over a 4 Å molecular sieve.

The liquid phase is separated from the molecular sieve and the remaining solvent is then driven off on a rotary evaporator. 183 mg (0.512 mmol) of pure 3-phenyl-3-benzoylamino-2-(1-ethoxyethoxy)propionic acid are obtained in the form of a white solid. The yield is 68%.

The product obtained is in the form of an equimolecular mixture of the two epimers (determination by the proton nuclear magnetic resonance spectrum).

3-Phenyl-3-benzoylamino-2-(1-ethoxyethoxy)propionic acid has the following characteristics:
  melting point: 93°–94° C.
  optical rotation: $[\alpha]^{25}_D = -21.2°$ (c=0.69, methanol)
  infrared spectrum (film): principal characteristic absorption bands at 3425, 3600–2100, 3060, 3025, 2975, 2925, 1740, 1640, 1600, 1580, 1520, 1480, 1440, 1300, 1140, 1075, 1020, 950, 920, 865, 800, 765 and 700 cm$^{-1}$
  proton nuclear magnetic resonance spectrum (300 MHz; CDCl₃; chemical shifts in ppm; coupling constants J in Hz): 0.90 and 1.07 (2t, J=7, 3H); 1.24 (d, J=5.3, 3H); 2.88–2.99 and 3.24–3.45 (2m, 2H); 4.50 and 4.63 (2d, J=2.4, 1H); 4.60 and 4.81 (2q, J=5.3, 1H); 5.74–5.80 (m, 1H); 7.26–7.52 (m, 8H); 7.78–7.83 (m, 2H); 7.0–7.8 (s broad, 1H)

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process for the enantioselective preparation of phenylisoserine derivatives of formula (I)

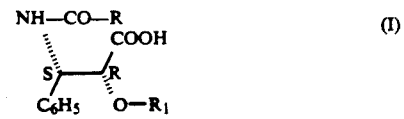

in which R is a phenyl or tert-butoxy radical and R₁ is a protecting group for the alcohol group, comprising treating S(+)-phenylglycine with a reducing agent and an agent for introducing a benzoyl or t-butoxycarbonyl group to give an alcohol of formula V

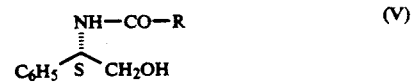

in which R is as defined above, which is oxidized and then reacted with a vinylmagnesium halide to give a product of the formula (VI)

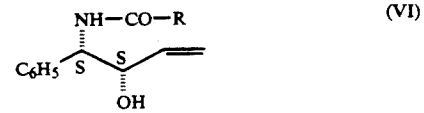

in which R is as defined above, the hydroxyl group of which is then protected by a group $R_1$ to give a product of formula (VII)

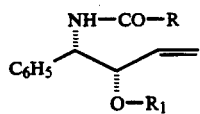

in which R and $R_1$ are as defined above, which is oxidized to the product of formula (I).

2. Process according to claim 1 for the preparation of a product of formula (I) wherein $R_1$ is a protecting group for the alcohol group selected from methoxymethyl, 1-ethoxyethyl, benzyloxymethyl, (b-trimethylsilylethoxy)methyl, tetrahydropyranyl and 2,2,2-trichloroethoxycarbonyl radicals.

3. Process according to claim 1, wherein the S(+)-phenylglycine is reduced by means of a reducing agent selected from lithium aluminum halide and borane ($BH_3$), optionally in the form of a complex with dimethyl sulphide, and a reagent for introducing a benzoyl or t-butoxycarbonyl group is then reacted with the amino alcohol obtained.

4. Process according to claim 3, wherein the reagent for introducing a t-butoxycarbonyl group is di-t-butyl dicarbonate.

5. Process according to claim 3, wherein the reagent for introducing a benzoyl group is benzoyl chloride.

6. Process according to claim 1, wherein the S(+)-phenylglycine is treated with a reagent for introducing a benzoyl or t-butoxycarbonyl group, and the acid obtained is then reduced by means of a reducing agent selected from lithium aluminum hydride and borane ($BH_3$), optionally in the form of a complex with dimethyl sulphide.

7. Process according to claim 6, wherein the reagent for introducing a t-butoxycarbonyl group is di-t-butyl dicarbonate.

8. Process according to claim 6, wherein the reagent for introducing a benzoyl group is benzoyl chloride.

9. Process according to claim 1, wherein 2-phenyl-2-5-butoxycarbonylaminoethanol or 2-phenyl-2-benzoylaminoethanol is oxidized by means of an oxalyl chloride/dimethyl sulphoxide mixture, and the aldehyde obtained as an intermediate is then reacted with a vinylmagnesium halide to give 1-phenyl-1-t-butoxycarbonylamino-2- hydroxybut-3-ene or 1-phenyl-1-benzoylamino-2-hydroxybut-3-ene, the hydroxyl group of which is protected in accordance with known methods of preparing ethers and acetals.

10. Process according to claim 1, wherein 1-phenyl-1-t-butoxycarbonylamino-2-hydroxybut-3-ene or 1-phenyl-1-benzoylamino-2-hydroxybut-3-ene, the hydroxyl group of which is protected, is oxidized by means of an alkali metal periodate in the presence of a catalytic amount of a ruthenium salt, or by means of potassium permanganate, and the phenylisoserine derivative of formula (I is then isolated.

* * * * *